United States Patent [19]

Rycheck et al.

[11] 4,188,501

[45] Feb. 12, 1980

[54] PURIFICATION OF MONOOLEFIN-CONTAINING HYDROCARBON STREAM

[75] Inventors: Mark R. Rycheck; Filippo Pennella, both of Bartlesville, Okla.

[73] Assignee: Phillips Petroleum Company, Bartlesville, Okla.

[21] Appl. No.: 936,954

[22] Filed: Aug. 25, 1978

[51] Int. Cl.$^2$ .................... C07C 3/62; C10G 29/16
[52] U.S. Cl. ..................... 585/643; 208/89; 208/283; 208/295; 208/296; 585/854
[58] Field of Search ............ 260/683 D, 677 A; 208/283, 295, 296, 89

[56] References Cited

U.S. PATENT DOCUMENTS

| | | | |
|---|---|---|---|
| 2,378,969 | 6/1945 | Bailey | 260/677 |
| 2,413,871 | 1/1947 | Hepp | 208/262 |
| 3,660,506 | 5/1972 | Banks et al. | 260/666 |
| 3,784,676 | 1/1974 | Moss | 423/242 |
| 3,883,566 | 5/1975 | Johnson | 260/346.1 |
| 3,998,902 | 12/1976 | Foster et al. | 260/677 A |

*Primary Examiner*—George Crasanakis

[57] ABSTRACT

Purity of hydrocarbon streams is increased by contacting with stable oxides of calcium, titanium, zinc, or zirconium prior to passage to a catalytic conversion process. In one embodiment, the stable metal oxides are preactivated by heating with vaporous hydrocarbon at an elevated temperature which is effective in extending the temperature at which metal oxides are subsequently effective for purification of hydrocarbon streams.

10 Claims, No Drawings

PURIFICATION OF MONOOLEFIN-CONTAINING HYDROCARBON STREAM

This invention relates to an improved process for the purification of hydrocarbon streams. In accordance with another aspect, this invention relates to a process for the removal of catalyst poisons from hydrocarbon streams by contacting with at least one metal oxide of calcium, titanium, zinc, or zirconium. In accordance with another aspect, the stable metal oxides are improved in activity for removal of catalyst poisons by preactivating with vaporous hydrocarbon to be treated prior to contacting with a hydrocarbon stream for purification. In accordance with another aspect, this invention relates to process for the purification of olefin-containing streams by contacting with stable oxides of calcium, titanium, zinc or zirconium prior to being subjected to disproportionation in the presence of a disproportionation catalyst.

The principal object of the present invention is to provide an improved method of removing catalyst poisons from hydrocarbons.

Another object is to effect the removal of catalyst poisons from hydrocarbon reactants more simply, more economically, and more effectively than by previously proposed processes.

Another object of this invention is to effect an improvement in the art of removal of catalyst poisons by means of adsorbents.

Another object of this invention is to provide an improved method of activating adsorbents effective for the removal of catalyst poisons from hydrocarbon streams.

Other objects, aspects, as well as the several advantages of the invention will be apparent to those skilled in the art upon reading the specification and the appended claims.

In accordance with the invention, the purity of hydrocarbon streams is increased by contacting with at least one stable oxide of calcium, titanium, zinc or zirconium at an elevated temperature not exceeding about 300° C.

In accordance with one embodiment, catalyst poisons present in hydrocarbon streams being fed to a catalytic conversion process are removed by contacting with at least one stable oxide of calcium, titanium, zinc or zirconium at a temperature not exceeding about 300° C. for a period of time sufficient to yield a hydrocarbon stream substantially free of catalyst poisons, and then subjecting the hydrocarbon stream substantially free of catalyst poisons to catalytic conversion such as disproportionation, polymerization, and the like.

In accordance with another embodiment, the effectiveness of the oxides of calcium, titanium, zinc or zirconium for removing catalyst poisons from hydrocarbon streams is improved by preactivating the metal oxide by contacting with vaporous hydrocarbon at an elevated temperature, and allowing the preactivated oxides to cool to ambient conditions prior to being contacted with a hydrocarbon stream for removal of catalyst poisons. It has been found that the temperature range at which these metal oxides are effective to purify hydrocarbon streams is extended due to preactivation with a vaporous hydrocarbon.

The adsorbents of this invention that are effective are occasionally found as naturally occurring minerals of sufficient purity to be immediately usable after activation. More frequently, and preferably, the adsorbents have been synthesized under conditions in which their purity, surface area, and physical form can be controlled. Purity, while not defined numerically, should be such that no other component will adversely affect the hydrocarbon reaction. The surface area should be at least about one square meter per gram, and the physical form should permit good contact between fluid and adsorbent without causing excessive pressure drop.

Calcium oxide can conveniently be made by calcination of naturally occurring limestone or dolomitic limestone, or by calcination of precipitated chalk. Complete conversion of carbonate to the oxide is not required although the oxide is believed to be the effective agent. The (generally) powdery oxide is tableted or pelleted for convenience in use, suitable care being taken to avoid excessive recarbonation of the lime from atmospheric carbon dioxide.

Rutile, anatase, and brookite are forms of titanium dioxide that are suitable for use as an adsorbent of this invention. They may be prepared, e.g., by hydrolysis of titanium tetrachloride or titanyl sulfate, or by burning titanium tetrachloride in oxygen to produce titanium dioxide and chlorine. The gelatinous product from aqueous hydrolysis can, after drying, be used directly as an adsorbent, or powdered titanium dioxide can be compacted into tablets for convenience in use.

Zinc oxide, prepared commercially generally by burning zinc vapor in air, is a fine powder that preferably should be tableted or pelleted for convenience in use.

Zirconium dioxide can be prepared indirectly from zircon by dehydration of hydrous zirconium oxide to produce an effective adsorbent. As above, it can be tableted or pelleted for convenience in use.

Hydrocarbons amenable to purification by the adsorbents of this invention are paraffins (including naphthenes) and monoolefins. The upper limit on molecular weight of hydrocarbons that can be purified is determined by their volatility—it is required that hydrocarbons being treated should be in the vapor state. Thus $C_{10}$ molecules can be treated, but preferably the paraffins will range between methane and about $C_6$, and monoolefins will range between $C_2$ and about $C_6$. The olefins can be expected to undergo double bond isomerization during the purification procedure; their skeletal isomerization is much less probable. In contrast, no isomerization of paraffins occurs.

The process of purification taught by this invention must be considered as an empirical procedure, because available analytical methods have not been helpful to identify any materials removed by the adsorbents. For this reason, olefin disporportionation has provided the diagnostic method by which the efficacy of adsorbents was determined. The disproportionation reaction requires the substantial absence from the feed of impurities that can serve as catalyst poisons. Some of these, e.g., water, molecular oxygen, sulfur compounds, and halogen compounds are known; others are unknown. In evaluating the adsorbents of this invention, all known poisons were absent from the hydrocarbon. I.e., polymerization grade propylene was used, and it was always contacted, at ambient temperature, with activated 13X molecular sieve and activated magnesium oxide, before contacting the adsorbent being tested.

Adsorbent temperature is an important variable that determines its effectiveness. Optimum temperature ranges for the adsorbents that are disclosed here are similar, but vary slightly, and also vary depending on the manner in which the adsorbent has been activated. Conventional activation consists of heating the adsorbent to about 450°–550° C. in flowing air, primarily to dry it, but this treatment can also remove by oxidation carbonaceous material that may be present. At about the same temperature air is displaced by flushing with an inert gas, e.g., argon, nitrogen, etc., and the adsorbent is then cooled to the temperature at which it is to be used. The optimum temperature range is, broadly, from about 100°–300° C., and preferably the temperature will lie between about 150°–250° C.

With calcium oxide, zirconium dioxide, and zinc oxide an unexpected result in the manner of activation is the observation that if, after drying and flushing at 450°–550° C., the adsorbent is then contacted at about 4000 GHSV, 200°–300° C., for at least 30 minutes with vapor of the hydrocarbon that is to be treated, the temperature at which the adsorbent is very effective is increased by about 50° C., i.e., from about 100°–350° C. Thus, according to this embodiment of the invention the effectiveness of the solid metal oxide adsorbent for removal of catalyst poisons is increased by the steps of activating the adsorbent by heating with a gas, which is preferably an inert gas, at an elevated temperature, about 500° C., then treating the adsorbent at a temperature of 200°–300° C. with vapor of a hydrocarbon stream which can be the same stream as subsequently used for removal of catalyst poisons. The heating with the hydrocarbon vapor is discontinued and the adsorbent is allowed to cool to ambient conditions before initiating contacting with a hydrocarbon stream to be purified.

The pressure at which hydrocarbons can be purified by contacting these adsorbents is not critical, provided it is less than the vapor pressure at the temperature of treatment, i.e., assuring that the hydrocarbon remains in the vapor phase.

The contact time for treatment of hydrocarbons may be equivalent to a gas hourly space velocity (GHSV) as high as 20,000 hr.$^{-1}$. The GHSV should not exceed 10,000; preferably it will be less than 5000 hr.$^{-1}$. In general product purity can be expected to be directly proportional to contact time, i.e., inversely proportional to GHSV.

This invention can be illustrated with the following examples.

All experimental data were obtained in the following manner. Polymerization grade propylene, supplied at 10 psig from a stock cylinder via a pressure regulator, passed at ambient temperature through two steel pipe absorbers—the first containing about 250 ml of 13X molecular sieve and the second about 250 ml of tableted magnesium oxide. Both of these materials had been activated by being dried at 500° C. in flowing, dry air, then cooled under nitrogen and loaded into the pipe absorbers in a controlled atmosphere glove box containing high purity argon. Propylene from the MgO absorber, controlled by a fine metering valve, flowed at atmospheric pressure through two quartz reactors in series. Each was ½" o.d.×14" long, and contained a thermowell to permit measurement, with a thermocouple, of the temperature of the contained solid; each was in a separate electrically heated and temperature controlled furnace. The first reactor contained adsorbent being evaluated and the second contained 2.5 wt. % $WO_3$ on silica gel olefin disproportionation catalyst. Effluent from the second reactor flowed through the sample loop of a GLC analyzer and finally to a soap film flow meter. Propylene was kept completely out of contact with rubber or plastic materials until it had left the second reactor because these materials generally will add catalyst poisons.

During the runs the temperature of the second reactor, containing the olefin disproportionation catalyst, was always maintained at 400° C. At that temperature the thermodynamic equilibrium for the reaction 2 propylene $\rightleftarrows$ ethylene+butene-2 is reached at about 41 percent conversion. Meanwhile the temperature of the first reactor could be controlled independently to determine the effect of adsorbent temperature on the activity of the disproportionation catalyst.

EXAMPLE 1

Calcium oxide was prepared by mixing reagent grade powder with 5 wt. % of polyolefin powder as lubricant, then compacted into wafers by compressing at 10,000 psig. These were crushed and a $-20+40$ mesh U.S. sieve fraction was separated for the runs. Three ml (2.4 gm) of CaO were placed in the first reactor and it was activated in place by heating in flowing air for about one hour at 500° C., then purging with nitrogen while cooling to ambient temperature. Flow of propylene through both reactors at 200 ml/min was started, and the following data were collected, in the order in which they are listed.

Table I

| Run | Temp. of CaO, °C. | Product Analysis, Mole % | | | | Conversion, % |
|---|---|---|---|---|---|---|
| | | $C_2H_4$ | $C_3H_6$ | $t$-$C_4H_8$-2 | $c$-$C_4H_8$-2 | |
| 1 | 25 | 0.9 | 97.5 | 0.8 | 0.8 | 2.5 |
| 2 | 100 | 8.8 | 76.1 | 7.9 | 7.2 | 23.9 |
| 3 | 200 | 10.5 | 70.5 | 10.2 | 8.8 | 29.5 |
| 4 | 300 | 10.3 | 70.8 | 10.1 | 8.8 | 29.2 |
| 5 | 400 | 3.6 | 89.8 | 3.3 | 3.3 | 10.2 |
| 6 | 100 | 10.1 | 71.7 | 9.7 | 8.5 | 28.3 |

Between about 100°–300° C. the CaO is effective to permit nearly 30 percent conversion of propylene, while outside that range (Runs 1 and 5) conversion was markedly lower.

EXAMPLE 2

Calcium oxide was activated by heating in air, then purging with nitrogen, as in example 1; however, in this instance, when the CaO had cooled to 300° C. the flowing nitrogen was replaced with 200 ml/min. propylene, and the following data were collected, in the order in which they are listed.

Table II

| Run | Temp. of CaO, °C. | Product Analysis, Mole % | | | | Conversion, % |
|---|---|---|---|---|---|---|
| | | $C_2H_4$ | $C_3H_6$ | $t$-$C_4H_8$-2 | $c$-$C_4H_8$-2 | |
| 7 | 300 | 13.8 | 63.5 | 12.5 | 10.2 | 36.5 |
| 8 | 30 | 13.4 | 62.6 | 13.4 | 10.6 | 37.4 |
| 9 | 100 | 13.9 | 61.4 | 13.8 | 10.9 | 38.6 |
| 10 | 300 | 14.3 | 60.7 | 14.0 | 11.0 | 39.3 |
| 11 | 350 | 14.1 | 60.7 | 14.2 | 11.0 | 39.3 |
| 12 | 400 | 9.1 | 74.3 | 8.7 | 7.9 | 25.7 |
| 13 | 300 | 13.4 | 63.0 | 13.2 | 10.4 | 37.0 |

After activation with propylene at 300° C., the calcium oxide effectively purified it between 30°–350° C.; only at 400° C. (Run 12) was a reduction in effectiveness apparent.

EXAMPLE 3

With the reactor containing disproportionation catalyst removed from use, calcium oxide was activated as in example 2, including the treatment with propylene. At 4000 GHSV propylene feed rate the calcium oxide was evaluated at 30°, 100°, 200°, 300°, and 400° C.; no evidence of olefin disproportionation was obtained, showing that this adsorbent was not active for conversion.

EXAMPLE 4

Zirconium dioxide, from Harshaw Chemical's Zr-030-4 T ⅛ E 149-1-105 pellets, was crushed and a −10+40 mesh U.S. sieve fraction was separated for the runs. Three ml (4.8 gm) were placed in the first reactor and activated in flowing air at 500° C. for 20 minutes, and flushed with nitrogen while cooling to 100° C. Propylene was introduced at 4000 GHSV, and the following data were collected, in the order in which they are listed.

Table III

| Run | Temp. of $ZrO_2$, °C. | Product Analysis, Mole % | | | | Conversion, % |
|---|---|---|---|---|---|---|
| | | $C_2H_4$ | $C_3H_6$ | t-$C_4H_8$-2 | c-$C_4H_8$-2 | |
| 14 | 23 | 2.0 | 94.4 | 1.8 | 1.8 | 5.6 |
| 15 | 100 | 9.4 | 73.7 | 8.9 | 8.0 | 26.3 |
| 16 | 200 | 10.3 | 71.4 | 9.7 | 8.6 | 28.6 |
| 17 | 300 | 10.4 | 71.2 | 9.8 | 8.6 | 28.8 |
| 18 | 350 | 5.7 | 84.3 | 5.1 | 4.9 | 15.7 |
| 19 | 400 | 0.9 | 97.5 | 0.8 | 0.8 | 2.5 |
| 20 | 200 | 11.0 | 69.5 | 10.4 | 9.1 | 30.5 |

Between about 100°–300° C. zirconium dioxide is effective to permit about 26–29 percent conversion of the propylene, while outside that temperature range (Runs 14 & 19) conversion was markedly lower.

Zirconium dioxide alone was evaluated for disproportionation activity by activating as described in example 3, then contacting with propylene at 23°, 100°, 200°, 300°, and 400° C. No evidence of olefin disproportionation was obtained at any temperature.

EXAMPLE 5

Degussa titanium dioxide powder (anatase) was prepared by compressing at 10,000 psig, then crushing the resulting wafers and separating a −10+80 mesh U.S. sieve fraction. Three ml (2.6 gm) were loaded into the first reactor and activated by heating in flowing air for one hour at 500° C., purging at that temperature with nitrogen for 15 minutes, and cooling. At 50° C. the flow of propylene was started at 4000 GHSV, and the following data were collected, in the order in which they are listed.

Table IV

| Run | Temp. of $TiO_2$, °C. | Product Analysis, Mole % | | | | Conversion, % |
|---|---|---|---|---|---|---|
| | | $C_2H_4$ | $C_3H_6$ | t-$C_4H_8$-2 | c-$C_4H_8$-2 | |
| 21 | 50 | 4.3 | 88.1 | 3.8 | 3.8 | 11.9 |
| 22 | 100 | 12.4 | 65.2 | 11.3 | 11.1 | 34.8 |
| 23 | 150 | 14.7 | 60.3 | 14.0 | 11.0 | 39.7 |
| 24 | 250 | 14.8 | 60.3 | 14.0 | 10.9 | 39.7 |
| 25 | 225 | 12.4 | 66.8 | 11.3 | 9.5 | 33.2 |
| 26 | 250 | 11.2 | 69.1 | 10.6 | 9.1 | 30.9 |
| 27 | 350 | 0.3 | 99.5 | 0.1 | 0.1 | 0.5 |
| 28 | 300 | 3.4 | 90.6 | 3.0 | 3.0 | 9.4 |
| 29 | 250 | 9.8 | 72.9 | 9.1 | 8.2 | 27.1 |
| 30 | 200 | 11.7 | 67.7 | 11.1 | 9.5 | 32.3 |
| 31 | 150 | 12.7 | 65.8 | 11.7 | 9.8 | 34.2 |

Between about 100°–250° C. titanium dioxide is effective to permit 30–40% conversion of propylene. It is impaired more at higher temperatures than calcium or zirconium oxides.

Titanium dioxide alone was evaluated for disproportionation activity by activating it as described for calcium oxide in example 3, then testing with propylene at 50°, 100°, 150°, 200°, 250°, 300°, and 350° C. No evidence of olefin disproportionation was obtained at any temperature.

EXAMPLE 6

Zinc oxide, available as ¼″×¼″ tablets, was prepared by crushing, then separating a −10+40 mesh U.S. sieve fraction. Three ml (3.5 gm) were loaded into the first reactor and activated by heating in flowing air for one hour at 500° C., purging at that temperature with flowing nitrogen for about 30 minutes, then cooling to ambient temperature. At 25° C. the flow of propylene was started over the zinc oxide at 4000 GHSV and the following data were collected, in the order in which they are listed.

Table V

| Run | Temp. of ZnO, °C. | Product Analysis, Mole % | | | | Conversion, % |
|---|---|---|---|---|---|---|
| | | $C_2H_4$ | $C_3H_6$ | t-$C_4H_8$-2 | c-$C_4H_8$-2 | |
| 32 | 25 | 9.8 | 74.4 | 8.4 | 7.4 | 25.6 |
| 33 | 100 | 13.1 | 65.4 | 11.8 | 9.7 | 34.5 |
| 34 | 200 | 13.6 | 64.0 | 12.4 | 10.0 | 36.0 |
| 35 | 300 | 3.6 | 91.2 | 2.6 | 2.6 | 8.8 |
| 36 | 350 | 0.4 | 98.8 | 0.4 | 0.4 | 1.2 |
| 37 | 100 | 12.9 | 65.8 | 11.7 | 9.6 | 34.2 |

Between about 100°–200° C. zinc oxide was particularly effective to purify propylene. Above 300° C. (Runs 35 & 36) it was seen to fail rapidly as a purifying agent, but effectiveness returned when cooled to 100° C.

In another set of runs, the activation of zinc oxide was started as described above. However, after purging about 30 minutes at 500° C. with nitrogen the reactor was cooled to 200° C., and nitrogen was replaced with propylene at that temperature for about 90 minutes before cooling to ambient temperature and collecting the following measurements, in the order in which they are listed.

Table VI

| Run | Temp. of ZnO, °C. | Product Analysis, Mole % | | | | Conversion, % |
|---|---|---|---|---|---|---|
| | | $C_2H_4$ | $C_3H_6$ | t-$C_4H_8$-2 | c-$C_4H_8$-2 | |
| 38 | 25 | 15.0 | 59.3 | 14.7 | 11.0 | 40.7 |
| 39 | 100 | 15.0 | 59.3 | 14.7 | 11.0 | 40.7 |
| 40 | 200 | 15.1 | 59.2 | 14.7 | 11.0 | 40.8 |
| 41 | 250 | 13.5 | 62.8 | 13.2 | 10.5 | 37.2 |
| 42 | 300 | 6.3 | 82.3 | 5.8 | 5.6 | 17.7 |
| 43 | 100 | 14.8 | 59.5 | 14.6 | 11.1 | 40.5 |

Activation of the zinc oxide with propylene, as described, increased its effectiveness at temperatures both below and above the 100°–200° C. range that had previously been optimum.

Zinc oxide alone was evaluated for disproportionation activity after activating it as outlined in the first part of this example. It was contacted with propylene at 4000 GHSV at 25°, 100°, 200°, and 300° C. No evidence of olefin disproportionation was obtained at any temperature.

EXAMPLE 7

A control run pertinent to all prior examples was made in which propylene purified only by activated 13X molecular sieve and magnesium oxide at ambient temperature, was disproportionated at 400° C. at the same space velocity that was used in all preceding examples. In this run, after 192 minutes on stream, conversion by disproportionation was 11.7 percent.

EXAMPLE 8

Additional runs were made using silica—both low and high surface area—to evaluate its effectiveness to purify propylene as indicated by the disproportionation reaction. Both kinds of silica were activated identically before evaluating. Three ml of quartz chips (low S.A.) or Davison −20+40 mesh silica gel (high S.A.) were heated in the first reactor in flowing air for about an hour at 500° C., purged with nitrogen at that temperature for about 30 minutes, and cooled to ambient temperature. Propylene was introduced at 4000 GHSV and the following data were collected with the crushed quartz adsorbent.

Table VII

| Run | Temp. of Quartz, °C. | Product Analysis, Mole % | | | | Conversion, % |
|---|---|---|---|---|---|---|
| | | $C_2H_4$ | $C_3H_6$ | $t\text{-}C_4H_8\text{-}2$ | $c\text{-}C_4H_8\text{-}2$ | |
| 44 | 23  | 1.8 | 95.1 | 1.5 | 1.6 | 4.9 |
| 45 | 100 | 1.9 | 94.7 | 1.7 | 1.7 | 5.3 |
| 46 | 200 | 2.1 | 94.3 | 1.8 | 1.8 | 5.7 |
| 47 | 300 | 2.2 | 93.8 | 2.0 | 2.0 | 6.2 |
| 48 | 400 | 5.4 | 85.1 | 4.8 | 4.7 | 14.9 |
| 49 | 200 | 2.4 | 93.3 | 2.1 | 2.2 | 6.7 |

Similarly silica gel was evaluated as an adsorbent in the first reactor and the following data were collected.

Table VIII

| Run | Temp. of silica Gel, °C. | Product Analysis, Mole % | | | | Conversion, % |
|---|---|---|---|---|---|---|
| | | $C_2H_4$ | $C_3H_6$ | $t\text{-}C_4H_8\text{-}2$ | $c\text{-}C_4H_8\text{-}2$ | |
| 50 | 25  | 2.0 | 94.4 | 1.8 | 1.8 | 5.6 |
| 51 | 100 | 3.0 | 91.5 | 2.7 | 2.8 | 8.5 |
| 52 | 200 | 3.9 | 89.1 | 3.5 | 3.5 | 10.9 |
| 53 | 300 | 5.1 | 85.6 | 4.7 | 4.6 | 14.4 |
| 54 | 400 | 4.4 | 87.6 | 4.0 | 4.0 | 12.4 |
| 55 | 200 | 6.2 | 82.7 | 5.7 | 5.4 | 17.3 |

It is evident that neither form of silica is comparable to the adsorbents disclosed in this invention in their optimum temperature range, demonstrating that merely raising the temperature of the propylene in the first reactor is much less effective than contacting it with calcium oxide, zirconium dioxide, zinc oxide, or titanium dioxide at temperatures that have been disclosed in these examples.

As disclosed hereinbefore and as demonstrated by the specific working examples, this invention sets forth effective methods for increasing the purity of hydrocarbon streams, particularly paraffins and olefins, by contacting with stable oxides of calcium, titanium, zinc or zirconium. Moreover, the method of purifying hydrocarbon streams to remove catalyst poisons was discovered in connection with pretreatment of feedstocks for an olefin disproportionation reaction and the instant process has been demonstrated in the working examples to facilitate that reaction. Reaction conditions, catalysts and other information pertinent to olefin disproportionation are disclosed in U.S. Pat. No. 3,660,506 which is incorporated herein by reference. The instant process of purifying hydrocarbon streams also can be easily applied to the pretreatment of hydrocarbon feedstocks for other hydrocarbon reactions e.g., polymerization of olefins, and the like.

We claim:

1. A process for the removal of catalyst poisons from hydrocarbons which comprises contacting under vapor phase conditions a monoolefin-containing hydrocarbon stream contaminated with catalyst poisons with a solid adsorbent selected from the group consisting of the stable oxides of calcium, titanium, zinc and zirconium at a temperature not exceeding about 300° C. and for a period of time sufficient to yield an olefin-containing stream substantially free of said catalyst poisons.

2. A process according to claim 1 wherein said olefin stream freed of catalyst poisons is passed directly to an olefin disproportionation process wherein said stream is contacted with a disproportionation catalyst under disproportionation conditions to produce an increased yield of higher and lower boiling disproportionated olefin products.

3. A process according to claim 1 wherein the effectiveness of said solid adsorbent for removing catalyst poisons is increased for said contacting by pretreating with vapors of said olefin-containing stream at a temperature in the range of about 200°–300° C., and allowing said heated adsorbent to cool to ambient conditions before initiating said contacting.

4. A process according to claim 1 for increasing the effectiveness of said adsorbent by heating with an inert gas at an elevated temperature, discontinuing heating with said gas and allowing said adsorbent to cool to ambient conditions, heating said cooled adsorbent with vapor of said olefin-containing stream at a temperature in the range of 200°–300° C., and discontinuing heating with said vapor and allowing said adsorbent to cool to ambient conditions before initiating said contacting.

5. A process according to claim 1 wherein said monoolefin-containing stream is propylene and the temperature of said contacting is in the range of about 150° to about 250° C.

6. A process according to claim 5 wherein the propylene stream substantially free of catalyst poisons removed from said contacting is passed directly to a disproportionation zone and therein contacted with a disproportionation catalyst under disproportionation conditions to produce increased yields of ethylene and butene.

7. A process according to claim 1 wherein the temperature of said contacting is in the range of about 100° to about 300° C.

8. A process according to claim 1 wherein said monoolefin-containing stream is polymerization grade propylene, the temperature of said contacting is in the range of about 100° to about 300° C., and the propylene stream substantially free of catalyst poisons removed from said contacting is passed directly to a disproportionation zone and therein contacted with a disproportionation catalyst comprising tungsten oxide-silica under reaction conditions which produce increased yields of ethylene and butenes.

9. A process according to claim 1 wherein said hydrocarbon stream consists essentially of a mixture of monoolefins and paraffins.

10. A process according to claim 3 wherein said adsorbent is activated by heating with air at a temperature in the range of about 450°–550° C. to dry said adsorbent prior to said pretreating step.

* * * * *